US011911594B2

(12) United States Patent
Lekkala et al.

(10) Patent No.: US 11,911,594 B2
(45) Date of Patent: Feb. 27, 2024

(54) SYSTEMS AND APPARATUS FOR DRIP RATE MEASUREMENT FOR MEDICAL FLUID ADMINISTRATION

(71) Applicant: CareFusion 303, Inc., San Diego, CA (US)

(72) Inventors: Niranjan Lekkala, Chinchwad (IN); Kanjimpuredathil Muralikrishna Menon, Bangalore (IN); Thotapalli Suryakiran, Bangalore (IN)

(73) Assignee: CareFusion 303, Inc., San Diego, CA (US)

( * ) Notice: Subject to any disclaimer, the term of this patent is extended or adjusted under 35 U.S.C. 154(b) by 679 days.

(21) Appl. No.: 17/085,816

(22) Filed: Oct. 30, 2020

(65) Prior Publication Data

US 2022/0133995 A1     May 5, 2022

(51) Int. Cl.
*A61M 5/168*     (2006.01)
*A61M 5/14*     (2006.01)

(52) U.S. Cl.
CPC ........ *A61M 5/1689* (2013.01); *A61M 5/1411* (2013.01); *A61M 2205/3327* (2013.01);
(Continued)

(58) Field of Classification Search
CPC ............ A61M 5/1689; A61M 5/16895; A61M 5/1411; A61M 2205/3327;
(Continued)

(56) References Cited

U.S. PATENT DOCUMENTS 2,068,135 A * 1/1937 Howse .................... G01F 23/02
                                                         73/299
4,670,007 A * 6/1987 Wheeldon ............. A61M 5/172
                                               128/DIG. 13
(Continued)

FOREIGN PATENT DOCUMENTS

| | | | | |
|---|---|---|---|---|
| FR | 2273264 A | * | 1/1976 | ........ A61M 5/16813 |
| FR | 2398177 A | * | 3/1979 | ............. F01D 17/02 |
| IN | 201841001942 A | * | 1/2018 | .......... A61M 39/281 |

OTHER PUBLICATIONS

Gayathri, et al., "Automatic indication system of glucose level in glucose trip bottle," International Journal of Multidisciplinary Research and Modern Education (IJMRME) 725, ISSN (Online): 2454-6119, (www.rdmodernresearch.org) vol. 3, Issue 1, 2017.
(Continued)

*Primary Examiner* — Nathan R Price
*Assistant Examiner* — Mark A Igel
(74) *Attorney, Agent, or Firm* — Morgan Lewis & Bockius LLP

(57) ABSTRACT

A system for measuring drip rate may include a drip chamber device comprising an elongated body including an inner surface defining a chamber, and a drip rate measurement device. The drip chamber may be fluidly coupled to a container containing an IV fluid configured to drip droplets of the IV fluid into the chamber. The drip rate measurement device may include a housing configured to be mounted to the elongated body of the drip chamber, and a load cell transducer mounted in the elongated body and extending into the chamber. The load cell transducer may be configured to measure a weight of the droplets of the IV fluid and convert the weight into an electrical signal. The drip rate measurement device may further include a controller electrically coupled to the load cell transducer to process the (Continued)

electrical signal and output at least one parameter associated with the IV fluid.

20 Claims, 3 Drawing Sheets

(52) U.S. Cl.
CPC ............... *A61M 2205/3334* (2013.01); *A61M 2205/3379* (2013.01); *A61M 2205/583* (2013.01)

(58) Field of Classification Search
CPC .. A61M 2205/3334; A61M 2205/3379; A61M 2205/583
See application file for complete search history.

(56) References Cited

U.S. PATENT DOCUMENTS

| | | | | | |
|---|---|---|---|---|---|
| 4,889,528 | A | * | 12/1989 | Nadai | ............... A61M 5/16895 604/65 |
| 6,606,905 | B2 | * | 8/2003 | Carroll | ................... G01G 17/04 73/299 |
| 9,199,036 | B2 | * | 12/2015 | Kolko | ..................... G16H 20/17 |
| 2010/0114027 | A1 | * | 5/2010 | Jacobson | ............ A61M 5/1407 604/151 |
| 2011/0196304 | A1 | * | 8/2011 | Kramer | ............... A61M 5/1483 604/151 |
| 2011/0205074 | A1 | * | 8/2011 | Feng | .................. A61M 5/16845 340/613 |
| 2012/0289928 | A1 | * | 11/2012 | Wright | ................ A61M 1/3626 604/67 |
| 2016/0158442 | A1 | * | 6/2016 | Voigt | .................. A61M 5/1723 702/50 |
| 2016/0287785 | A1 | * | 10/2016 | Isaacson | ........... A61M 5/16895 |
| 2018/0256817 | A1 | * | 9/2018 | Ohwada | ............ A61M 5/16804 |
| 2019/0015589 | A1 | * | 1/2019 | Shtram | .................. A61M 5/172 |
| 2021/0128815 | A1 | * | 5/2021 | Byrne | .................... A61B 1/015 |

OTHER PUBLICATIONS

Sardana, et al., "Design, Fabrication, and Testing of an Internet Connected Intravenous Drip Monitoring Device," Molecular Diversity Preservation International; Journal of Sensor and Actuator Networks, Dec. 2018.

Kamble, et al., "Monitoring of Intravenous Drip Rate," Proceedings of ICBME, Dec. 21-24, 2001.

Thariyan, et al., "Design and Development of a Unique Drop Sensing Unit for Infusion Pump," Journal of Scientific & Industrial Research; vol. 61, Oct. 2002, pp. 798-801.

International Search Report and Written Opinion for Application No. PCT/US2021/057036, dated Feb. 22, 2022, 14 pages.

* cited by examiner

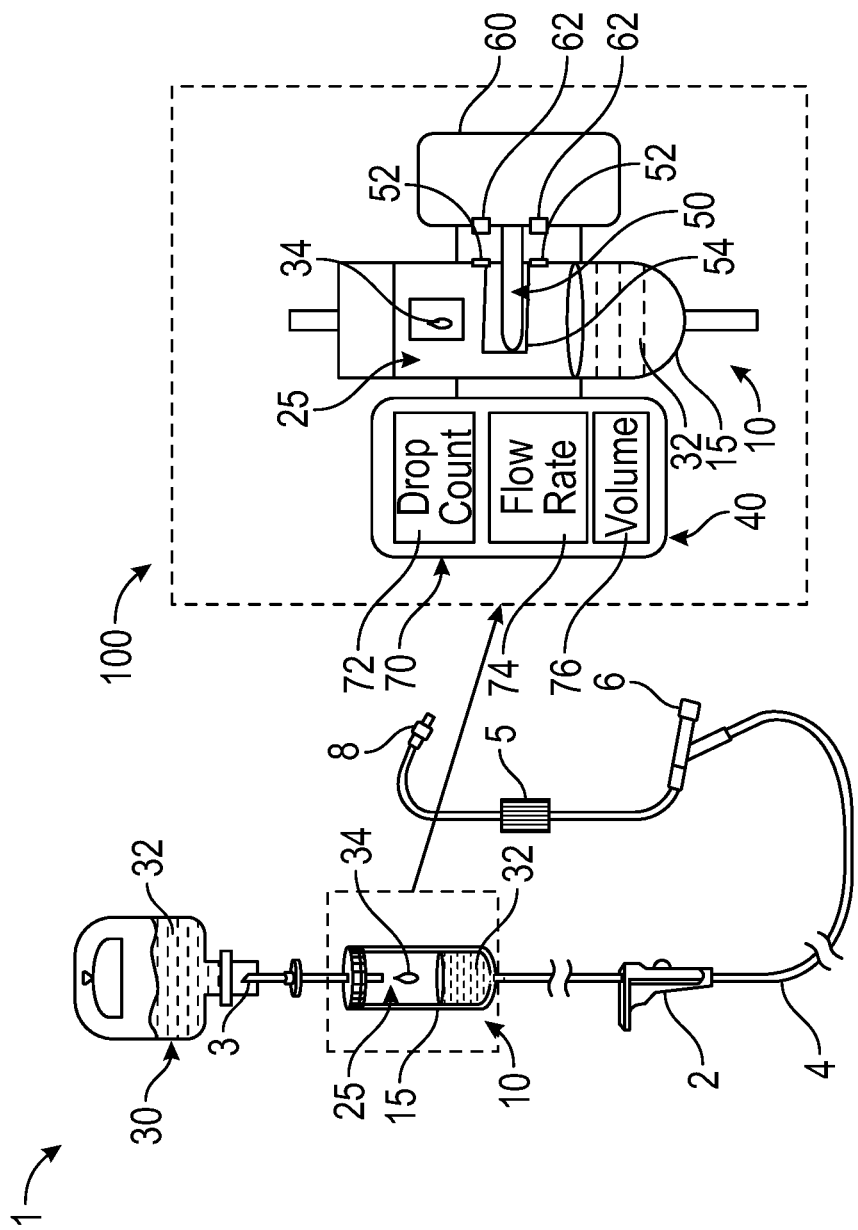

SYSTEMS AND APPARATUS FOR DRIP RATE MEASUREMENT FOR MEDICAL FLUID ADMINISTRATION

TECHNICAL FIELD

The present disclosure generally relates to administration of parenteral fluids to a patient by means of an intravenous (IV) set, and particularly to an improved IV drip rate measurement system and associated drip chamber for use in an IV fluid administration system.

BACKGROUND

An IV set for the administration of parenteral fluids generally comprises a drip chamber, a length of clear plastic tubing attached to the discharge end of the drip chamber, one or more clamps to adjust the fluid flow through the clear tubing and a means at the distal end of the tubing for mounting a hypodermic needle which will be inserted into the patient's vein or artery. The drip chamber is generally cylindrically shaped and is provided with a pointed hollow element (i.e., piercing element) at the top thereof, which is adapted to pierce the rubber or elastomeric seal on an inverted bottle of parenteral fluid in order to drain the fluid therefrom into the drip chamber. The cylindrical wall of the drip chamber is formed from clear plastic material in order to detect fluid dripping into the chamber.

Fluid flow to the patient is usually determined by detecting the number of drops of fluid which fall into the drip chamber over a period of time and then multiplying the number of drops by a standard number used for the volume of each drop. When this method of flow rate detection is done manually, it is frequently inaccurate as a result of human error. Furthermore, continuous monitoring can be time consuming.

The description provided in the background section should not be assumed to be prior art merely because it is mentioned in or associated with the background section. The background section may include information that describes one or more aspects of the subject technology.

SUMMARY

In accordance with various embodiments of the present disclosure, a system for measuring drip rate may include a drip chamber device comprising an elongated body including an inner surface defining a chamber, and a drip rate measurement device. The drip chamber may be fluidly coupled to a container containing an IV fluid configured to drip droplets of the IV fluid into the chamber. The drip rate measurement device may include a housing configured to be mounted to the elongated body of the drip chamber, and a load cell transducer mounted in the elongated body and extending into the chamber. The load cell transducer may be configured to measure a weight of the droplets of the IV fluid and convert the weight into an electrical signal. The drip rate measurement device may further include a controller electrically coupled to the load cell transducer to process the electrical signal and output at least one parameter associated with the IV fluid.

In accordance with various embodiments of the present disclosure, a system for measuring drip rate of an IV fluid may include a drip chamber fluidly coupled to a container containing the IV fluid configured to drip droplets of the IV fluid into an interior of the drip chamber. The drip chamber may include an aperture extending laterally from an outer surface of a sidewall of the drip chamber to the interior of the drip chamber. A drip rate measurement device may be detachably coupled to the drip chamber. The drip rate measurement device may include a housing, a load cell transducer mounted on the housing. The load cell transducer may extend into the drip chamber via the aperture when the drip rate measurement device is coupled to the drip chamber. The load cell transducer may be configured to measure a weight of the droplets of the IV fluid and convert the weight into an electrical signal. A controller may be electrically coupled to the load cell transducer to process the electrical signal and output at least one parameter associated with the IV fluid.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 1 illustrates an IV set that includes a drip chamber device, in accordance with some embodiments of the present disclosure.

FIG. 2A illustrates a front view of a system for measuring drip rate, in accordance with some embodiments of the present disclosure.

DETAILED DESCRIPTION

Figure 2B:
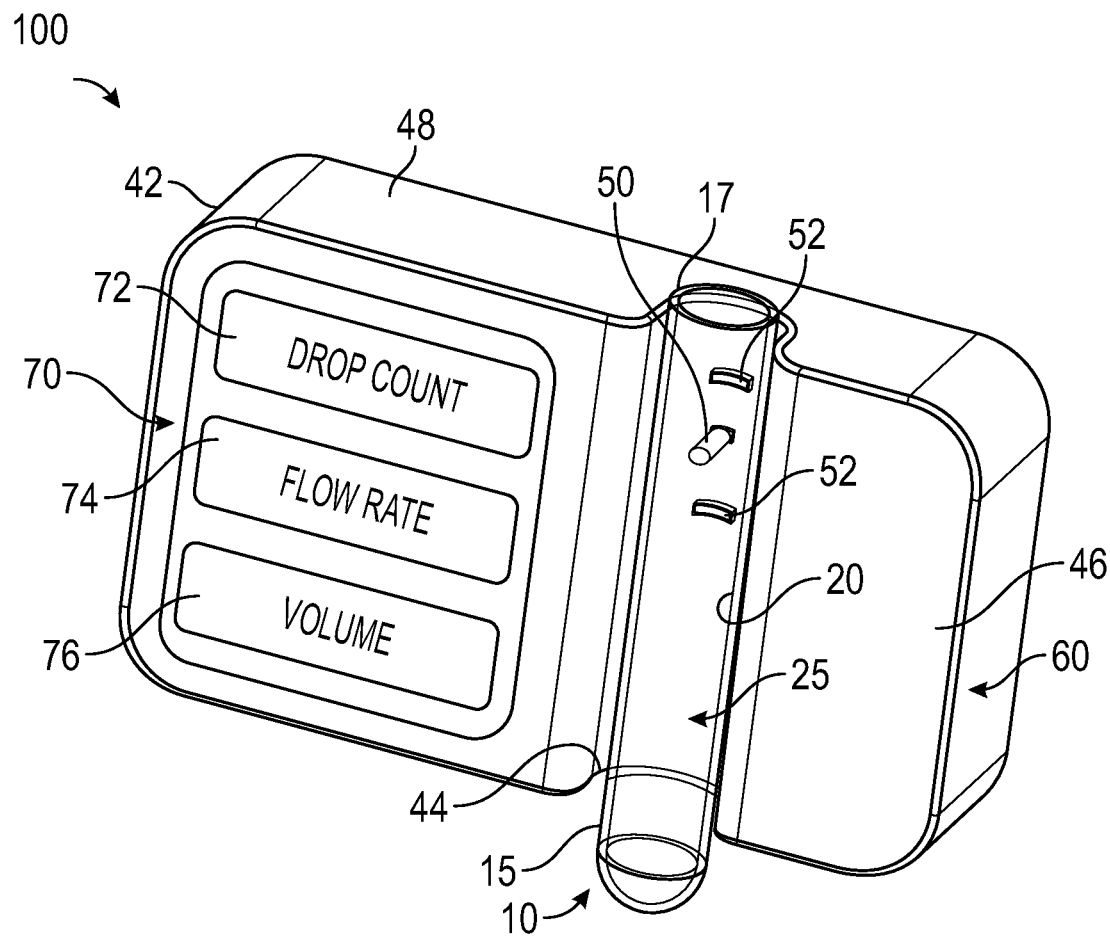
FIG. 2B illustrates a perspective view of a system for measuring drip rate, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to administration of parenteral fluids to a patient by means of an intravenous (IV) set, and particularly to an improved IV drip rate measurement system and associated drip chamber for use in an IV fluid administration system. In particular, various embodiments of the present disclosure are directed to providing a system for measuring drip rate including a drip chamber device having an elongated body including an inner surface defining a chamber, and a drip rate measurement device. The drip chamber may be fluidly coupled to a container containing an IV fluid configured to drip droplets of the IV fluid into the chamber. The drip rate measurement device may include a housing configured to be mounted to the elongated body of the drip chamber, and a load cell transducer mounted in the elongated body and extending into the chamber. In some embodiments, the load cell transducer may be a strain gauge-based load cell transducer. The strain gauge-based load cell transducer may be configured to measure a weight of the droplets of the IV fluid and convert the weight into an electrical signal. The drip rate measurement device may further include a controller electrically coupled to the load cell transducer to process the electrical signal and output at least one parameter associated with the IV fluid, in particular the drip rate of the IV fluid.

Accordingly, the systems and apparatuses for monitoring and for measuring drip rate of an IV fluid of the various embodiments described herein are advantageous in utilizing a strain gauge-based load cell transducer that accurately bases the drip rate on actual weight of the droplet versus basing the drip rate on droplet count. The aforementioned configuration is advantageous as compared with the currently existing systems and apparatus for measuring drip or drop rate as these do not measure actual weight of the droplets. Instead, the currently existing systems and apparatuses use infrared (IR) or other optical sensors to count the droplets and track the intervals between the drops to determine flow rate. This method is not always accurate because the size and volume of droplets dripping into the drip chamber may vary over time due to factors such as variance in the specific gravity, viscosity, density, pressure and gravity at the IV fluid bag or container. Accordingly, the currently existing systems, devices, and methods which calculate drip rate without taking into consideration actual weight of each droplet may inaccurately lead to over-or under estimation of the IV fluid drip or drop rate.

FIG. 1 illustrates a multiple line IV extension set 1 that includes a drip chamber device 10 in accordance with some embodiments of the present disclosure. The IV set 1 may include an IV bag 30 containing parenteral fluid hanging from an IV stand (not shown). The IV set 1 as illustrated may include a drip chamber device 10, tubing 4, a roller clam 2 for manual flow control, a Y-site connector, a filter 5, and an adapter or luer 8 for coupling the tubing 4 to a needle or catheter at the distal end of tubing 4. As depicted, the drip chamber device 10 may generally be in the form of a clear plastic, hollow, cylindrical elongated body 15. An upper portion of the body 15 may be provided with a pointed piercing element or spike 3 adapted to be inserted through a pierceable seal of the IV bag 30 to drain the fluid 32 therein through drop former 17. In some embodiments, the elongated body 15 may include an inner surface 20 defining a chamber 25. As illustrated, the drip chamber 15 may be fluidly coupled to a container, for example, IV bag 30 that is configured to drip droplets 34 of the IV fluid 32 into the chamber 25.

FIG. 2A illustrates a front view of a system for measuring drip rate, in accordance with some embodiments of the present disclosure. FIG. 2B illustrates a perspective view of a system for measuring drip rate, in accordance with some embodiments of the present disclosure. Referring to FIGS. 2A and 2B, a system 100 for measuring drip rate may include the drip chamber device 10 and a drip rate measurement device 40. In some embodiments, the drip rate measurement device 40 may include a housing 42 configured to be mounted to the elongated body of the drip chamber. For example, the housing 42 may include recessed portion or groove 44 extending longitudinally from an upper surface 48 to a lower surface 49 of the housing 42. A diameter or radius of the recessed portion or groove 44 may correspond to an outer diameter of the elongate body 15 of the drop chamber device 10 such that the housing 42 may be mounted to a sidewall of the elongate body 15, as illustrated in FIG. 2B.

In some embodiments, the drip rate measurement device 40 may further include a load cell transducer 50 mounted in the elongated body 15 and extending laterally into the chamber 25. As shall be described in further detail below, the load cell transducer 50 may be configured to measure a weight of the droplets 34 of the IV fluid 32 and convert the weight into an electrical signal. In some embodiments, as shall be described in further detail below, the drip rate measurement device may include a controller 86 (illustrated in FIG. 4) or similar processor electrically coupled to the load cell transducer 50 to process the electrical signal and output at least one parameter associated with the IV fluid 32.

In accordance with various embodiments of the present disclosure, the load cell transducer 50 may be a strain gauge-based load cell transducer. As depicted, the strain gauge-based load cell transducer may be in the form of an elongate body extending laterally or transversely into the chamber 25. In operation, as the droplets flow from the drop former 17 onto the strain gauge-based load cell transducer 50, the strain gauge-based load cell transducer 50 may deform under weight/force applied due to the weight of the droplet 34. The weight of the droplet 34 may be sensed or measured by the strain gauge-based load cell transducer 50. The strain associated with the weight of the droplet 34 applied to the strain gauge-based load cell transducer 50 may be converted into an electrical signal by the strain gauge-based load cell transducer 50. As shall be described in further detail below, the controller 86 may process the electrical signal and output at least one parameter associated with the IV fluid. The cumulative incremental in weight over time may be processed into parameters such as drop count/drip rate, flow rate and volume of drug. Accordingly, the controller may calculate and output a more accurate drop count, volume and flow rate of the IV fluid based on actual weight of the drops measured by the strain gauge-based load cell transducer 50. The aforementioned configuration is advantageous as compared with the currently existing systems and apparatus for measuring drip or drop rate as these do not measure actual weight of the droplets. Instead, the currently existing systems and apparatuses use infrared (IR) or other optical sensors to count the droplets and track the intervals between the drops to determine flow rate. This method is not always accurate because the size and volume of droplets dripping into the drip chamber may vary over time due to factors such as variance in the specific gravity, viscosity, density, pressure and gravity at the IV fluid bag or container. Accordingly, the currently existing systems, devices, and methods which calculate drip rate without taking into consideration actual weight of each droplet may inaccurately lead to over-or under estimation of the IV fluid drip or drop rate.

In some embodiments, the strain gauge-based load cell transducer 50 may be coated with one or more of an acrylic, an epoxy, or polyurethane. The aforementioned configuration may be advantageous in preventing patients and hospital staff from inadvertently suffering electrical shock from the load cell transducer 50.

In some embodiments, the strain gauge-based load cell transducer 50 may have a rounded geometry profile. For example, as illustrated in FIG. 2B, the strain gauge-based load cell transducer 50 may have a cylindrical shape. The aforementioned configuration may be advantageous in to preventing stagnation of drops on load cell, which may otherwise interfere with accuracy of the data.

In some embodiments, the strain gauge-based load cell transducer 50 may be formed of a material capable of withstanding temperature ranges from 5 to 50 degrees Celsius without affecting its droplet weight measuring capability. For example, in some embodiments the strain gauge-based load cell transducer may be formed of a material including, but not limited to one or more of Ferritic steel, Austenitic steel, and Titanium.

In accordance with various embodiments of the present disclosure, the drip rate measurement device 40 may include a printed circuit board (PCB) 60 disposed in the housing 42 of the drop measurement device 40. The controller 86 may be disposed on the PCB 60. For example, in some embodiments the controller may be etched or soldered onto the PCB 60. In some embodiments, several other components may be disposed on the on the PCB for processing of the analog signal generated by the strain gauge-based load cell transducer 40. In some embodiments, the PCB 60 may be a single chip PCB.

As depicted, the strain gauge-based load cell transducer 50 may include terminal points 52 for electrically coupling the strain gauge-based load cell transducer 50 to the PCB 60 and related components, e.g. the controller 86. Similarly, the housing 42 may include corresponding terminal points 62 through which the PCB 60 and related components, e.g. the controller 86 are electrically coupled to the strain gauge-based load cell transducer 50. As depicted, terminal points 62 may be disposed at the recessed portion or groove 44 at a position on a front face 46 of the housing 42 corresponding to the positions of the terminal points 52 on the elongate body so as to allow electrical coupling of components of the PCB 60, e.g., controller 86 to the strain gauge-based load cell transducer 50.

Figure 3A:
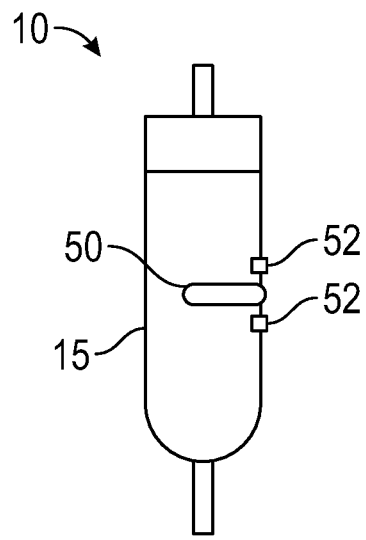
FIG. 3A illustrates a drip chamber device with an integrated load cell transducer, in accordance with some embodiments of the present disclosure.

FIG. 3A illustrates a drip chamber device with an integrated load cell transducer 50, in accordance with some embodiments of the present disclosure. As illustrated in FIG. 3A, in some embodiments, the strain gauge-based load cell transducer 50 may be integrated in the elongate body 15 of the drip chamber device 10. For example, the strain gauge-based load cell transducer 50 may be fixedly mounted or integrally formed with the elongated body 15 of the drip chamber device 10. In these embodiments, the terminal points 52 of the strain gauge-based load cell transducer 50 may be fixedly positioned on or in a sidewall of the elongate body 15 of drip chamber device 52. In these embodiments, terminal points 52 may be fixedly coupled to the sidewall of the elongate body 15 via a plastic welding or other joining method. For example, the terminal points 52 may be fixed to the drip chamber 10 by ultrasonic welding.

Figure 3B:
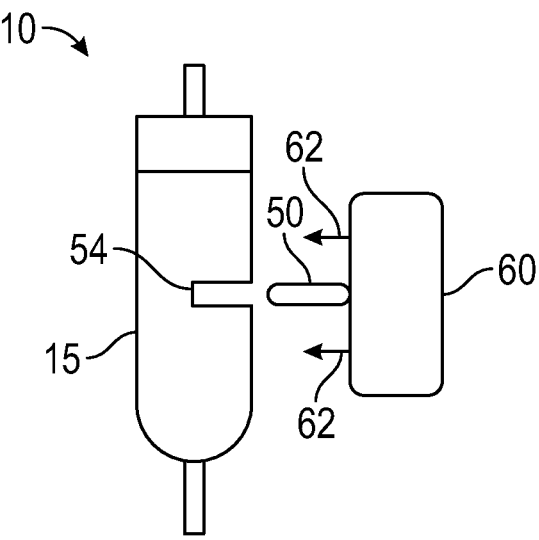
FIG. 3B illustrates a drip chamber device with an integrated load cell transducer which is detachably coupleable to the drip chamber, in accordance with some embodiments of the present disclosure.

FIG. 3B illustrates a drip chamber device with an integrated load cell transducer 50 which is detachably coupleable to the drip chamber 10, in accordance with some embodiments of the present disclosure. As illustrated in FIG. 3A, in some embodiments, the strain gauge-based load cell transducer 50 may be a separate component that is detachably coupleable to the drip chamber 10. In these embodiments, the drip chamber device 10 may include an aperture 54 extending laterally from an outer surface of a sidewall of the elongate body 15 of drip chamber device 10. As depicted, the aperture 54 may extend to the interior of the drip chamber device 10 to allow the strain gauge-based load cell transducer 50 to be detachably mounted therein. In these embodiments, the strain gauge-based load cell transducer 50 may be coupled to the housing 42.

Referring back to FIGS. 2A and 2B, according to various aspects of the present disclosure, the drip rate measurement device 40 may further include a display device 70 electrically coupled to and communicated with the PCB. For example, the display device may be a Graphical User Interface (GUI) display configured to display at the at least one parameter (e.g., drop count/drip rate, flow rate and volume) calculated and output by the controller. The display device 70 may include at least one of a drop count display section 72 for displaying a drop count output transmitted from the controller, a flow rate display section 74 for displaying a flow rate output transmitted from the controller, or a volume display section 76 for displaying a volume output transmitted from the controller.

Figure 4:
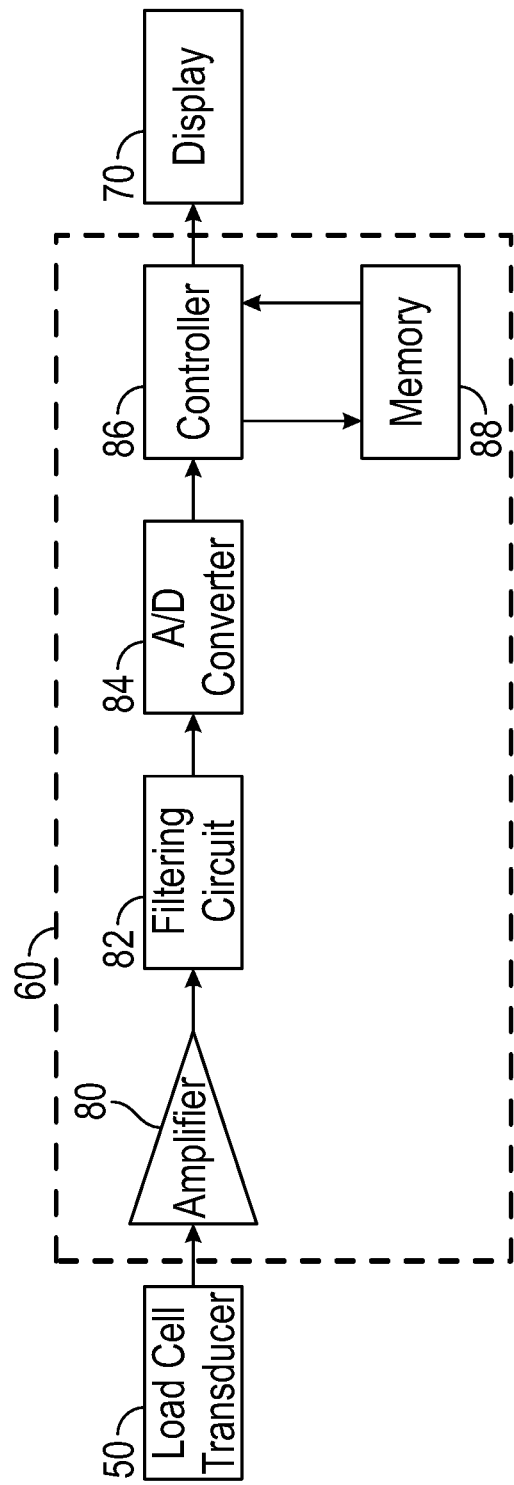
FIG. 4 is a block diagram showing the inter-relationship between various components of a drip rate measurement device, in accordance with some embodiments of the present disclosure.

FIG. 4 is a block diagram showing the inter-relationship between various components of a drip rate measurement device 100, in accordance with some embodiments of the present disclosure. As discussed, the strain gauge-based load cell transducer 50 may convert a change in force (i.e., strain), applied to the strain gauge-based load cell transducer 50 due to the weight of the droplet 34, into an analog electrical signal. The analog electrical signal may be inversely proportional to the force being measured. As depicted, the analog electrical signal may be amplified by an amplifier 80 and then fed into a filtering circuit 82 to filter out or remove any undesirable data or noise. The filtered signal may then be fed into an analog-to-digital converter (A/D Converter) 84, which converts the analog signal to a digital signal. In some embodiments, the amplifier 80, the filtering circuit 82, and the A/D Converter 84 may each be disposed on, etched on, or soldered to the PCB 60. The controller 86 may process the digital output data from the A/D Converter 84 and then transmit the converted data to the display device 70 for viewing. In some embodiments, the controller may exchange data with a memory storage device 88. The cumulative incremental in weight stored in the memory storage device 88 over time may be processed into accurate drop count/drip rate, flow rate and volume of the IV fluid.

Accordingly, the systems and apparatuses for monitoring and for measuring drip rate of an IV fluid of the various embodiments described herein are advantageous in utilizing a strain gauge-based load cell transducer, which accurately bases the drip rate on actual weight of the droplet versus basing the drip rate on droplet count. The aforementioned configuration is advantageous as compared with the currently existing systems and apparatus for measuring drip or drop rate as these do not measure actual weight of the droplets. Instead, the currently existing systems and apparatuses use infrared (IR) or other optical sensors to count the droplets and track the intervals between the drops to determine flow rate. This method is not always accurate because the size and volume of droplets dripping into the drip chamber may vary over time due to factors such as variance in the specific gravity, viscosity, density, pressure and gravity at the IV fluid bag or container. Accordingly, the currently existing systems, devices, and methods which calculate drip rate without taking into consideration actual weight of each droplet may inaccurately lead to over-or under estimation of the IV fluid drip or drop rate.

Further, because a more accurate measurement of the infused IV fluid is possible using the system and apparatus of the various embodiments described herein, which provide an accurate IV fluid drip rate, errors associated with manually counting drops may be avoided. As described above, the drip rate is based on weight rather than drop count as traditionally done with currently existing systems.

Furthermore, the systems and apparatus of the various embodiments described herein are further advantageous in that because no manual counting of drops is necessary, no continuous monitoring of the IV fluid is required.

Additionally, the drip chamber and drip chamber devices of the various embodiments described herein may advantageously be used with any type of IV tubing (for example, either macrodrip tubing or microdrip tubing).

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A system for measuring drip rate, comprising:
    a drip chamber device configured to couple to a container containing an IV fluid, the drip chamber device comprising an elongated body including an inner surface defining a chamber, a load cell transducer mounted in the elongated body and extending laterally into the chamber, and a load cell transducer terminal point, the drip chamber device configured to receive drip droplets of the IV fluid into the chamber; and
    a drip rate measurement device comprising;
        a housing configured to be mounted to the elongated body of the drip chamber device;
        a drip rate measurement device terminal point to electrically couple with the load cell transducer terminal point when the elongated body is detachably mounted to the housing, wherein the load cell transducer configured to measure a weight of the droplets of the IV fluid and convert the weight into an electrical signal; and
        a controller electrically coupled to the load cell transducer to process the electrical signal and output at least one parameter associated with the IV fluid.

2. The system of claim 1, further comprising a display device electrically coupled to the controller to display the at least one parameter.

3. The system of claim 2, wherein the load cell transducer comprises a strain gauge-based load cell transducer.

4. The system of claim 3, wherein the strain gauge-based load cell transducer comprises an elongate body extending transversely into the chamber, the strain gauge-based load cell transducer configured to deform due to the weight of the droplets falling on the elongate body.

5. The system of claim 4, wherein the elongate body of the strain gauge-based load cell transducer comprises a cylindrical-shaped elongate body.

6. The system of claim 3, further comprising a printed circuit board (PCB) disposed in the housing of the drip rate measurement device, wherein the controller is disposed on the PCB.

7. The system of claim 6, wherein the load cell transducer comprises first and second load cell transducer terminal points, and the housing comprises corresponding first and second drip rate measurement device terminal points for electrically coupling the PCB to the load cell transducer.

8. The system of claim 7, further comprising an amplifier disposed on and electrically coupled to the PCB for amplifying the electrical signal.

9. The system of claim 7, further comprising an analogue-to-digital converter (A/D Converter) disposed on and electrically coupled to the PCB for converting the electrical signal from an analog to a digital signal.

10. The system of claim 7, further comprising a filtering circuit disposed on and electrically coupled to the PCB for removing undesirable data.

11. The system of claim 6, wherein the PCB comprises a single chip PCB.

12. The system of claim 2, wherein the display device comprises at least one of a drop count display section for displaying a drop count output transmitted from the controller, a flow rate display section for displaying a flow rate output transmitted from the controller, or a volume display section for displaying a volume output transmitted from the controller.

13. The system of claim 1, wherein the load cell transducer is detachably mounted in the elongated body of the drip chamber device.

14. The system of claim 1, wherein the load cell transducer is coated with at least one of an acrylic, an epoxy, or polyurethane.

15. The system of claim 1, wherein the drip rate measurement device terminal point is positioned in a recessed portion of the housing.

16. A system for measuring drip rate of an IV fluid, the system comprising:
    a drip chamber configured to fluidly couple to a container containing the IV fluid and receive drip droplets of the IV fluid into an interior of the drip chamber, the drip chamber comprising an aperture, extending laterally from an outer surface of a sidewall of the drip chamber to the interior of the drip chamber, a load cell transducer mounted in the interior, and a load cell transducer terminal point;
    a drip rate measurement device detachably coupled to the drip chamber, the drip rate measurement device comprising;
        a housing;
        a drip rate measurement device terminal point to electrically couple with the load cell transducer terminal point when the drip rate measurement device is detachably coupled to the drip chamber, the load cell transducer configured to measure a weight of the droplets of the IV fluid and convert the weight into an electrical signal; and
        a controller electrically coupled to the load cell transducer to process the electrical signal and output at least one parameter associated with the IV fluid.

17. The system of claim 16, further comprising a display device electrically coupled to the controller to display the at least one parameter.

18. The system of claim 17, wherein the load cell transducer comprises a strain gauge-based load cell transducer.

19. The system of claim 18, wherein the strain gauge-based load cell transducer comprises an elongate body extending transversely into the drip chamber, the strain gauge-based load cell transducer configured to deform due to the weight of the droplets falling on the elongate body.

20. The system of claim 16, wherein the at least one parameter comprises at least one of a drop count, a flow rate, or a volume of the IV fluid.

* * * * *